Figures 1, 2:
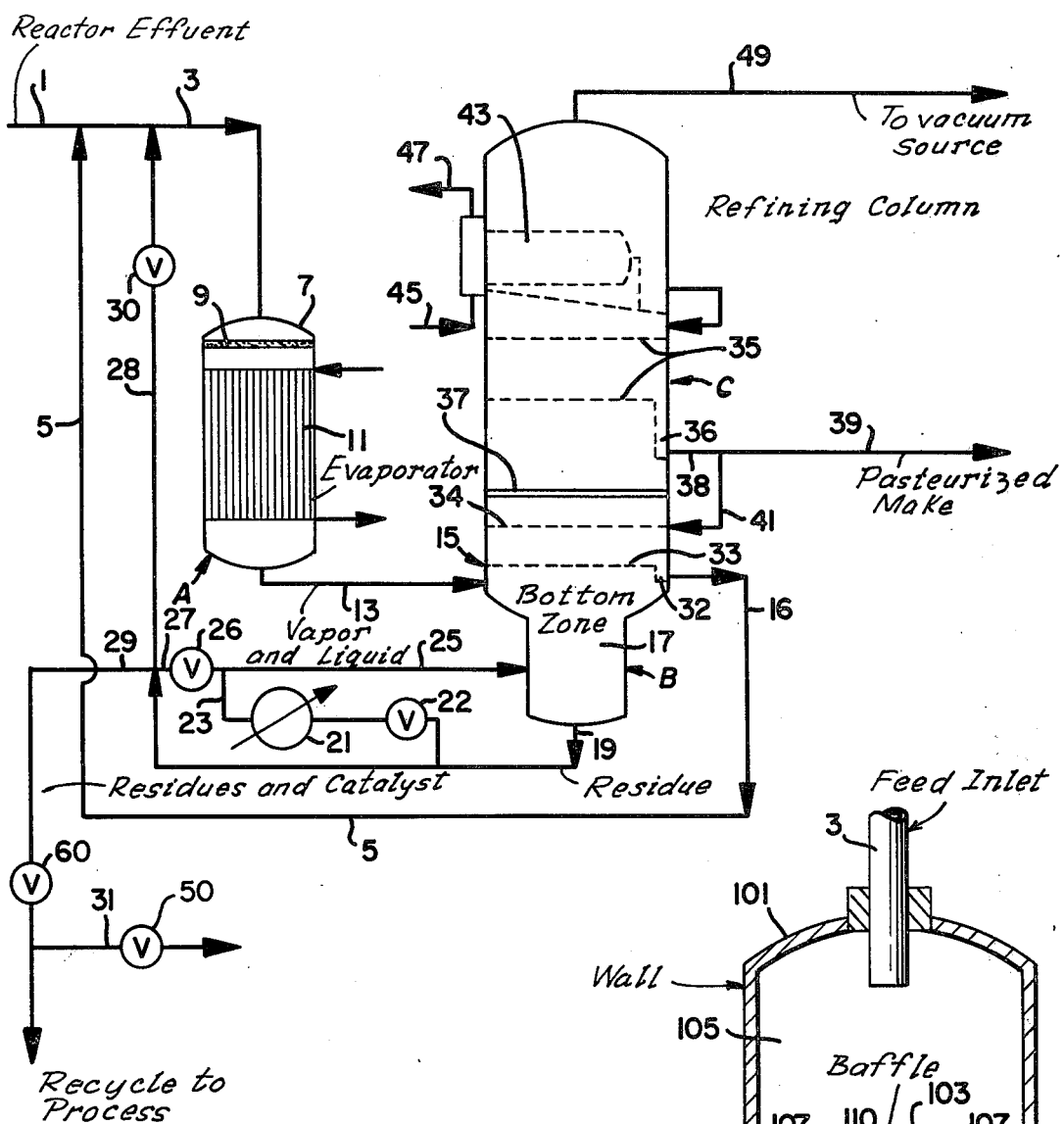

United States Patent [19]

Higley et al.

[11] 4,166,773

[45] Sep. 4, 1979

[54] CONTINUOUS PROCESS FOR SEPARATING HIGH BOILING, HEAT SENSITIVE MATERIALS

[75] Inventors: David P. Higley, Katonah, N.Y.; Gary L. Culp, Sissonville; John W. Crandall; Scott M. Farquhar, both of Charleston, all of W. Va.

[73] Assignee: Union Carbide Corporation, New York, N.Y.

[21] Appl. No.: 863,353

[22] Filed: Dec. 22, 1977

[51] Int. Cl.$^2$ ............................................. B01D 3/28
[52] U.S. Cl. ...................................... 203/72; 203/78; 203/98; 203/DIG. 19; 203/DIG. 25; 202/153; 260/340.2; 260/604 HF
[58] Field of Search .................... 203/72, 6, 89, 99, 98, 203/DIG. 19, 78, 80, 84, DIG. 25; 202/158, 153; 196/139, 128; 260/604 HF, 340.2

[56] References Cited

U.S. PATENT DOCUMENTS

| | | | |
|---|---|---|---|
| 1,744,421 | 1/1930 | Stroud | 203/98 |
| 2,337,489 | 12/1943 | Patterson | 203/98 |
| 2,664,391 | 12/1953 | Coulter | 203/98 |
| 2,713,023 | 7/1955 | Irvine | 203/83 |
| 2,900,312 | 8/1959 | Gilmore | 203/2 |
| 3,092,587 | 6/1963 | Ester et al. | 203/72 |
| 3,408,264 | 10/1968 | Ward | 203/98 |
| 3,531,376 | 9/1970 | Minoda et al. | 203/98 |
| 3,644,179 | 2/1972 | Knoer et al. | 203/72 |

Primary Examiner—Wilbur L. Bascomb, Jr.
Attorney, Agent, or Firm—Donald M. Papuga

[57] ABSTRACT

This invention is concerned with a continuous process for separating higher boiling, heat sensitive components from a liquid product stream. It involves a rapid evaporation of the desired product of the stream in an evaporator which minimizes residence time, such as a falling film evaporator, and feeding the vapors and the remainder of the stream to a separation column where the vaporized products rise in the column. Part of the vaporized products are removed after condensation and then recycled back to the column as a reflux. This reflux after contacting one or more trays is collected and recycled to the evaporator and mixed with the product feed being treated. The liquid remainder of the feed stream is collected at the bottom of the column. The bottom of the column can be kept at a temperature which minimizes any breakdown of the heat sensitive components present therein and, if desired, the bottoms in the column can be quickly withdrawn for treatment elsewhere or for recycling back to the process. A desirable embodiment is to recycle a portion of the residue at the bottom of the column back to the evaporator.

11 Claims, 2 Drawing Figures

Detail of Distributor for Falling Film Evaporator

CONTINUOUS PROCESS FOR SEPARATING HIGH BOILING, HEAT SENSITIVE MATERIALS

This invention relates to a continuous process of separating higher boiling heat sensitive components from a liquid product stream in which they are dissolved. In particular, this invention finds specific application in the separation of alkylene carbonates from catalyst containing streams in which they have been produced. Further embodiments of this invention involve the utilization of the separation process for separating complex rhodium containing catalysts utilized in the manufacture of aldehydes, such as described in U.S. Pat. No. 3,527,809 issued Sept. 8, 1970.

There are a number of chemical processes which utilize catalytic materials, which if present during the distillation of the products of reaction, are so heat sensitive as to become decomposed or enter into chemical reactions which are considered undesirable for their eventual reuse. There are other processes in which higher boiling heat sensitive components are present in a liquid product stream, which if heated during the distillation of the product stream enter into undesirable chemical reactions or acquire undesirable physical and/or chemical properties.

There are described in the literature processes for preparation of alkylene carbonates such as ethylene carbonate and propylene carbonate. For example, Peppel, *Industrial and Engineering Chemistry*, Vol. 50, No. 5, pp. 767–770 (May 1958), discloses a process for the manufacture of ethylene carbonate from the reaction of carbon dioxide with ethylene oxide utilizing tetraethylammonium bromide as the catalyst. As described in that article, the product of the reaction is distilled, apparently in a conventional fashion. It is known that commercial ethylene carbonate which is produced by the reaction of ethylene oxide with carbon dioxide utilizing this catalyst, possesses this catalyst in the composition. This renders the product, ethylene carbonate, undesirable for many uses since this catalyst impurity is unacceptable. In addition, failure to separate this catalyst from the ethylene carbonate represents loss of the catalyst from the process. Furthermore, it is known that during conventional distillation of ethylene carbonate containing this catalyst, a portion of the catalyst is decomposed by the heat applied, with the result that substantial amounts of the catalyst cannot be recovered. Also, ethylene carbonate decomposition is known to occur.

U.S. patent application, Ser. No. 683,534, filed May 5, 1976 describes a process for the manufacture of aldehydes by the hydroformylation of alpha-olefins of from about 2 to about 24 carbon atoms, or more. A particular important feature of the process is that it is effected utilizing higher boiling point condensation products of the aldehydes as a solvent for the catalyst. As a result, the catalyst is maintained in this reaction medium of condensation product even during distillation of aldehyde from the medium. However, one of the difficulties in effecting distillation of this type of system is that the catalyst, which is a rhodium phosphine carbonyl complex, tends to become unstable during the distillation even while it is kept in solution with these higher boiling condensation products. One of the advantages of the present invention is that such a product stream of aldehyde, and the condensation products, can be separated in accordance with the process of this invention, whereby the aldehyde products can be separately collected and the catalyst undergoes only minimum amount of heating during the separation step. As a result, catalyst decomposition is held to an absolute minimum.

The process of this invention can be more specifically characterized by reference to the drawing.

FIG. 1 represents a schematic side view of a refiner which employs the principals of the process of this invention. The refiner of FIG. 1 possesses three basic components, these are Component A, which is the evaporator, Component B, which is a bottom zone for collection of the liquid residue, and Component C which is a column which constitutes zones where rectification takes place.

With respect to FIG. 1, the stream containing the effluent from the reactor is characterized in Peppel, supra, or is described in copending application Ser. No. 863,352, filed on even date herewith, and now U.S. Pat. No. 4,117,250 or is described in copending U.S. patent application Ser. No. 683,534 filed May 5, 1976. Such reactor effluent which contains catalyst materials which are decomposable upon heating are supplied via line 1 to line 3 after being combined with recycle from line 5, as hereinafter described, and, optionally, recycle through line 28, as hereinafter defined. The combined feed, including recycle streams, constitute line 3, and is fed to evaporator 7. Evaporator 7 may be any type of evaporator which can effect a residence time which is short enough to avoid or minimize the degree of decomposition of the catalyst contained in the stream or any other component included in the stream which is supplied to the evaporator. Evaporator 7 may be a falling film evaporator, a wiped film evaporator, a thin film evaporator, a scraped surface type evaporator, and the like. Preference is given in the practice of this invention to the use of a falling film evaporator. However, this choice is based upon having more experience with this kind of evaporator and because of economic considerations.

Evaporator 7 may be of a number of different kinds of construction. FIG. 2 characterizes a side view of a cutaway portion of an evaporator which can be effectively utilized in the practice of this invention.

The evaporator shown in FIG. 1 differs somewhat in that it employs a perforated distributor plate 9 through which liquid is moved to the upper part of tubes 11. Evaporator 7 is jacketed and typically steam heated although any other heating fluid may be employed. The temperature of the evaporator is sufficient to effect evaporation of the product of the reaction which one wishes to recover while at the same time is insufficient to effect any significant amount of decomposition of any potentially decomposable material that is present, such as the catalyst product, or volatile components capable of entering into chemical reactions. The temperature selected is, of course, correlated with the residence time. This correlation allows, under some circumstances, one to utilize temperatures which if employed for over too long a period of time would cause the undesirable decomposition of the catalyst or other component, yet because of such short residence times, this decomposition will not occur to any significant degree.

The mixture of vapor and liquid which is removed from the bottom of the evaporator 7 is collected and transported through tube 13 into refining still 15. Refining still 15 contains two fundamental components, that is, residue collector B and rectification zone C. Pasteurization may also occur in zone C. As the liquid vapor mixture enters still 15, the liquid component is collected in base section 17. The refining still 15 and evaporator 7 possess the capability of being kept under vacuum via line 49. The rectification zone in still 15 contains one or more trays, 33 and 34, for example. Trays 33 and 34 serve the purpose of separating products from heavy components in the original stream and to separate a catalyst which can be entrained with the vapor. The remaining vapors generated via evaporator 7 pass up the distillation zone to condenser 43 which condenses the majority of the vapor. Non-condensable products are removed via line 49. In FIG. 1, the liquid from condenser 43 flows down the column through an optional pasteurization section (trays 35 serve as the pasteurization section to remove residual low boiling components if desired) to downcomer 36 and is collected in line 38. A portion of the material is removed as product via line 39. The remaining portion of liquid collected in downcomer 36 is returned to the column via line 41 to serve as reflux in the rectification zone. The still is provided with the demister pad 37 to assist in preventing catalyst losses and catalyst entrainment with the vapors rising in the still.

Liquid downflow from the rectification zone is totally collected via line 16 which removes total liquid product accumulated in downcomer 32.

Removal of liquid downflow totally from the process prevents dilution of the bottoms product so that the desired concentration of heavies can be achieved in the base of the column. The liquid downflow which is collected in line 16 is passed to line 5 for recycle back to the evaporator 7. As stated previously reactor effluent is combined with this recycle and the combination is supplied to evaporator 7.

Residue from the base is removed via line 19. If desired, the residue stream can be maintained at a cooler temperature by utilization of cooler 21. A portion of the residue stream can be recycled through the cooler via line 25 to provide the desired temperature in base section 17, to minimize the decomposition reaction. If necessary, a portion of the residue can be recycled via line 28 back to the evaporator so that the desired residue composition can be achieved in the base of the distillation column. The remaining residue is removed via line 29 and recycled to the process. A portion of the recycle is purged via valved line 31 as required. Flows for these options can be controlled by regulation of valves 22, 26, 30, 50 and 60.

As pointed out previously, with respect to the process of this invention, it is desirable to minimize the amount of decomposition in evaporator 7. Because the nature of reactor effluents which can be treated in accordance with this invention can vary, sometimes from batch to batch or from process to process, it is apparent that no specific residence time can be arbitrarily given as either a maximum or minimum in order to practice this invention. In the typical case it will be usual to utilize a residence time for evaporator 7 which will not exceed a maximum of one minute, and preferably, one which utilizes a maximum residence time of 30 seconds. In the most desirable embodiment of this process, the residence time would be less than about 20 seconds.

As a consequence of the process of this invention, the residue products which are collected in base 17, can be concentrated to a higher catalyst concentration for a fixed evaporator 7 operating temperature. Conversely, one can establish a fixed catalyst concentration that is desired for the residue collected in base 17, and as a consequence of this invention, the operating temperature of the evaporator 7 can be reduced because in a conventional system, wherein streams such as 16 and 19 would be combined, an evaporator such as evaporator 7 would have to operate at a higher temperature to achieve the desired catalyst concentration. Another advantage of the process of this invention, as is apparent from consideration of the process characterized in FIG. 1, is that for a fixed evaporator operating temperature, a lower purge rate from the bottom of the column results due to a higher catalyst/high boiling polymeric materials concentration in stream 19.

In the case where the process of this invention is employed for the separation of ethylene carbonate, reduction of the operating temperature of the evaporator for a fixed catalyst concentration, which as compared to a conventional process, will achieve a lowering in the rate of decomposition of the ethylene carbonate.

By virtue of the ability to maintain base 17 cooler than the temperature of the residue product which is dropped from the evaporator into the base, along with the short residence time in the evaporator, it is possible to significantly reduce both the decomposition of the catalyst such as employed by Peppel, supra, and as defined in copending application Ser. No. 863,352, and now U.S. Pat. No. 4,117,250 as well as the ethylene carbonate product. This feature of the invention is very significant when applied to the removal of aldehyde products from the reaction mixture taken from the reaction zone of the hydroformylation process as set forth in copending Application Ser. No. 556,270, filed Mar. 7, 1975 and now abandoned. Because of the short residence time in the evaporator, less aldehyde is self-condensed to increase the concentration of the higher boiling condensation products which serve the role as a solvent and at the same time maximizes the amount of aldehyde which can be recovered. In addition, the short residence time serves to minimize the potential for rhodium catalyst decomposition and losses of rhodium. As is well known, rhodium is an extremely costly material selling for as much as Five Hundred Dollars ($500.) a troy ounce. Therefore savings that can be derived by avoiding rhodium loss are extremely important, with respect to the commercial employment of such a hydroformylation process.

FIG. 2 characterizes one type of distributor for a falling film evaporator.

With respect to FIG. 2, the reactor effluent combined with recycled liquid are fed to the evaporator through line 3 into interior 105 of the evaporator. The evaporator is confined by wall 101. The liquid drops to the surface of baffle 103. Baffle 103 is circular and the liquid runs down through space 107, separating baffle 103 from wall 101. The liquid is then passed into space 108, through 108 and then into the interior of the distributor portion 110. When the liquid level rises to the surface of tubes 109, the liquid starts to run into the tubes in a thin film along the wall thereof. Space 115 is heated to cause evaporation, as previously stated. Thereafter the liquid and vaporized product mixture are collected in tube 13, as indicated in FIG. 1, and fed to still 15.

As an illustration of the operation of the process of this invention, the following example serves to demonstrate the various kinds of conditions which can be employed in practicing the process of this invention. In referring to these specific conditions, a reference will be made to FIG. 1 and the characterization of these conditions shall be in terms of the apparatus as depicted in FIG. 1. In still 15, the base 17 is maintained at 130° C. At 50 millimeters mercury pressure, cooler 21 is reducing the temperature of stream 19 to 100° C. and recycle is effected through line 25. The temperature of the vapor leaving the top tray of tray section 35 is 146° C. and is at a pressure of 36 millimeters mercury. The temperature of the water entering the condenser 43 through line 45 is 90° C. and is removed through line 47 at 110° C. The evaporator 7 is heated with 100 psig steam to 160° C. so that the liquid vapor mixture leaving via 13 is at 160° C. The feed rate through line 1 is 166.7 pounds per hour and comprises 94 weight percent ethylene carbonate, 1 weight percent tetraethyl ammonium bromide (TEAB) and 5 percent residues. The product rate removed via line 39 is 146.3 pounds per hour and comprises essentially 99.9 weight percent of ethylene carbonate and 0.1 weight percent of other materials. The composition of line 29 is 75 weight percent ethylene carbonate, 20 weight percent polymeric materials, and 5 weight percent TEAB. The composition of line 49 comprises 0.4 pounds per hour which breaks down to 19 weight percent ethylene oxide, 75 weight percent carbon dioxide and 6 weight percent of inert materials. The flow rate in line 41 is 30 pounds per hour and it is the same composition as characterized previously for line 39. Line 16 comprises 30 pounds per hour of essentially the same composition as in line 39, except the polymeric content is slightly higher.

Essentially 60 to 80 percent vaporization is effected per pass in evaporator 7. About 0.02 pounds per hour of the TEAB are decomposed and about 0.075 pounds per hour of the ethylene carbonate are decomposed. Approximately 50 weight percent of the ethylene oxide generated in the separation is reacted to polymer residue.

What is claimed is:

1. A continuous process of separating higher boiling, heat sensitive components from a liquid product stream in which they are dissolved, which comprises passing such stream to an evaporator which minimizes residence time whereby the desired product of the stream is vaporized with any light components contained therein, feeding both the vaporized products and the remainder of the stream to a distillation column where the vaporized products rise in the column and the liquid residue of the stream is collected in a bottom zone at the bottom of the column, the bottom of the column is kept at a temperature which minimizes any breakdown of the heat sensitive components present therein, providing a removal point within said column for removal of at least a portion of the condensate from the vaporized desired product from the column and recycling a portion of the desired product removed from the column back to the column at a point below said removal point and achieving a flux of such desired product at about where the desired portion is recycled back to the column, collecting at least a portion of said flux in said column as a liquid and recycling that liquid so collected to said evaporator and removing the liquid residue collected in the bottom zone at the bottom of the column from the column.

2. The process of claim 1, wherein at least a portion of the liquid residue is recycled from the bottom zone to said evaporator.

3. The process of claim 1, wherein the portion of the reflux collected in said column as a liquid is collected at a point in the column above where the vaporized feed is effected to said column.

4. The process of claim 1, wherein the residue stream is cooled.

5. The process of claim 4, wherein a portion of the cooled residue stream is recycled to the base of the column.

6. The process of claim 4, wherein a portion of the cooled residue stream is recycled to the evaporator.

7. The process of claim 1, wherein the evaporator is a falling film evaporator.

8. A continuous process of separating higher boiling, heat sensitive catalyst containing components from a liquid product stream in which they are dissolved, said product stream resulting from the production of alkylene carbonate by the reaction of alkylene oxide and carbon dioxide in the presence of a catalyst, which comprises passing such stream to an evaporator which minimizes residence time, whereby the desired product of the stream is vaporized with any light components contained therein, feeding both the vaporized products and the remainder of the stream to a distillation column where the vaporized products rise in the column and the liquid residue of the stream is collected in a bottom zone at the bottom of the column, the bottom of the column is kept at a temperature which minimizes any breakdown of the heat sensitive catalyst containing components present therein, providing a removal point within said column for removal of at least a portion of the condensate from the vaporized desired product from the column and recycling a portion of the desired product removed from the column back to the column at a point below said removal point and achieving a reflux of such desired product at about where the desired portion is recycled back to the column, collecting at least a portion of said reflux in said column as a liquid and recycling that liquid so collected to said evaporator and removing the liquid residue collected in the bottom zone at the bottom of the column from the column.

9. The process of claim 8, wherein the alkylene carbonate is ethylene carbonate.

10. A continuous process of separating higher boiling, heat sensitive catalyst containing components from a liquid product stream in which they are dissolved, said product stream resulting from the manufacture of aldehydes by the hydroformylation of alpha-olefins of from about 2 to about 24 carbon atoms in the presence of a catalyst, which comprises passing such stream to an evaporator which minimizes residence time, whereby the desired product of the stream is vaporized with any light components contained therein, feeding both the vaporized products and the remainder of the stream to a distillation column where the vaporized products rise in the column and the liquid residue of the stream is collected in a bottom zone at the bottom of the column, the bottom of the column is kept at a temperature which minimizes any breakdown of the heat sensitive catalyst containing components present therein, providing a removal point within said column for removal of at least a portion of the condensate from the vaporized desired product from the column and recycling a portion of the desired product removed from the column back to the column at a point below said removal point and achieving a reflux of such desired product at about where the desired portion is recycled back to the column, collecting at least a portion of said reflux in said column as a liquid and recycling that liquid so collected to said evaporator and removing the liquid residue collected in the bottom zone at the bottom of the column from the column.

11. The process of claim 10, wherein the manufacture of aldehydes is effected in a solvent of higher boiling point condensation products of the aldehydes.

* * * * *